United States Patent [19]

Choi et al.

[11] 4,079,038

[45] Mar. 14, 1978

[54] POLY(CARBONATES)

[75] Inventors: Nam Sok Choi, Chung Ryang, Seoul, South Korea; Jorge Heller, Palo Alto, Calif.

[73] Assignee: Alza Corporation, Palo Alto, Calif.

[21] Appl. No.: 664,127

[22] Filed: Mar. 5, 1976

[51] Int. Cl.$^2$ ............................................. C08G 63/62
[52] U.S. Cl. ......................... 260/47 XA; 260/77.5 D; 260/823; 427/214
[58] Field of Search ............ 260/77.5 D, 47 XA, 463, 260/823

[56] References Cited

U.S. PATENT DOCUMENTS 3,546,188  12/1970  Kesslin et al. ...................... 260/86.3

Primary Examiner—Theodore E. Pertilla
Attorney, Agent, or Firm—Paul L. Sabatine; Thomas E. Ciotti; Edward L. Mandell

[57] ABSTRACT

Poly(orthoester carbonates) and poly(orthocarbonate carbonates) having a repeating linear carbonate unit and a recurring symmetrical dioxycarbon moiety with a plurality of organic groups pendant from the carbon atom thereof are disclosed. The polymers are represented by the structural formula:

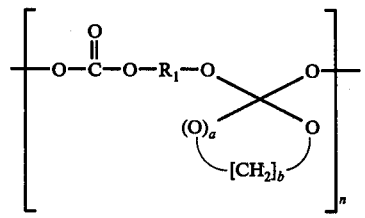

wherein $a$ is 0 to 1, $b$ is 2 to 6 when $a$ is 0, $b$ is 2 to 5 when $a$ is 1, and $n$ is greater than 10.

11 Claims, 1 Drawing Figure

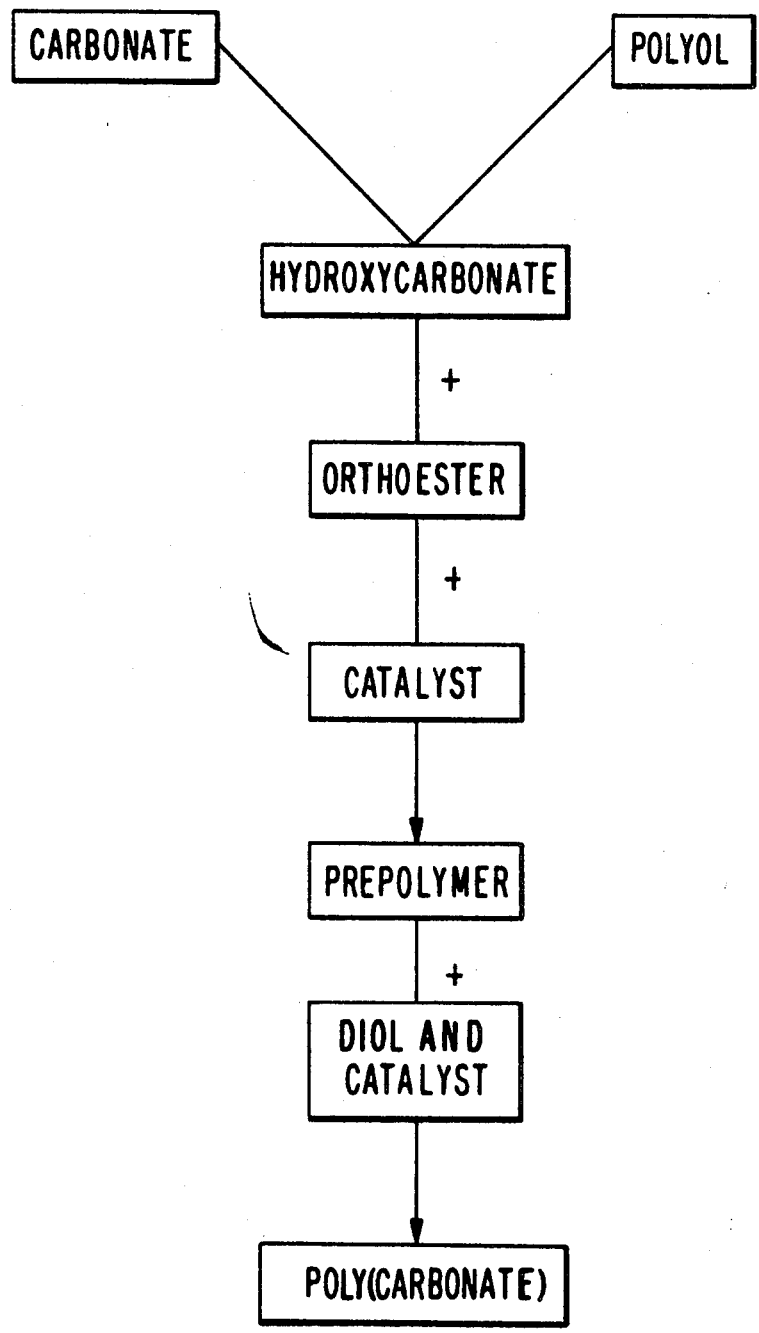

POLY(CARBONATES)

BACKGROUND OF THE INVENTION

This invention pertains to both novel and useful highly polymeric poly(carbonates). More particularly, the invention relates to poly(carbonates) having a number of carbonate units

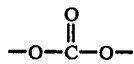

covalently bonded through a hydrocarbon group having a bivalent functionality to a repeating symmetrical dioxycarbon unit —O—C—O— having a multiplicity of organic groups pendant from the carbon atom thereof. The polymers of the invention are represented by the general formula as follows:

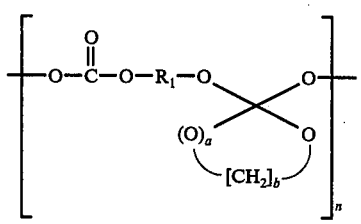

wherein $R_1$ is a member selected from the group consisting of alkylene; alkenylene; alkyleneoxa; alkenyleneoxa; cycloalkylene; cycloalkylene substituted with a member selected from the group consisting of alkyl, alkylene, alkenyl, alkenylene, and alkoxy; cycloalkenylene; cycloalkenylene substituted with a member selected from the group consisting of alkyl, alkylene, alkenyl, alkenylene, and alkoxy; arylene, and arylene substituted with a member selected from the group consisting of alkyl, alkylene, alkenyl, and alkoxy; $a$ is 0 and 1; $b$ is 2 to 6 when $a$ is 0, $b$ is 2 to 5 when $a$ is 1, and $n$ is at least 10, usually 10 to 5000. The polymers of the invention include copolymers of the random and block types formed by reacting monomers of preformed homopolymers, copolymers or oligomers, noncross-linked and cross-linked polymers.

DESCRIPTION OF THE PRIOR ART

The synthesis of poly(carbonates) is known to the prior art in U.S. Pat. No. 3,248,415 wherein poly(carbonates) are prepared by subjecting a mixture of an acylic 1,2-epoxide, carbon dioxide and a polyhydric alcohol to temperatures above 100° C to super atmospheric pressure in the presence of a base catalyst to yield poly(carbonates) of the structural formula:

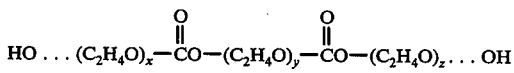

wherein $x$, $y$ and $z$ are greater than 1. Similarly, linear poly(carbonates) were prepared by the condensation of a glycol with an alkyl carbonate by Carothers as described in U.S. Pat. No. 2,789,968. Carothers, prepared poly(carbonates) by alcoholysis between a glycol and ethylcarbonate in the presence of an alkaline catalyst with alcohol driven off by heat. In U.S. Pat. No. 2,789,968, poly(carbonates) are produced by self-condensing a bis(carbonate) monomer:

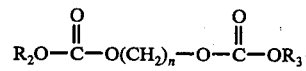

wherein $R_2$ and $R_3$ are alkyl or aryl, in the presence of an ester interchange catalyst as a condensing agent, at elevated temperature, and in an inert atmosphere with the latter part of the condensation conducted at low pressure to yield linear poly(carbonates) from said polymethylene glycol-bis-(alkyl or aryl carbonate). As seen from the above, the prior art provides a very specific poly(carbonate), and it did not provide any polymeric poly(carbonates) having both a carbonate and a dioxycarbon unit with organic groups pendant therefrom.

SUMMARY OF THE INVENTION

Accordingly, it is an immediate object of this invention to provide a new and useful class of polymeric polycarbonates having structural and physical embodiments that make the polymers a valuable contribution to the art and commerce.

It is a further object of this invention to provide novel polymeric carbonates comprising a backbone having a repeating carbonate unit and a recurring dioxycarbon unit with a multiplicity of organic groups bonded thereto. The polymers prepared according to the invention have a controlled degree of hydrophobicity with a corresponding controlled degree of erosion in aqueous or aqueous-like environments to innocuous products. The polymers are useful as coatings and they can be fabricated by conventional manufacturing techniques into assorted articles of manufacture having various useful shapes.

Yet still a further object of the invention is to provide poly(orthoester carbonates) that are easily synthesized at practicable rates and in controlled amounts.

Other objects, features, and advantages of the invention will be apparent to those skilled in the art from the detailed description of this specification, taken in conjunction with the flow chart and the accompanying claims.

SUMMARY OF FLOW CHART

The accompanying flow chart indicates a chemical process for synthesizing the poly(carbonates). The process comprises reacting a polyol with a carbonate to form a hydroxy substituted carbonate. The hydroxy substituted carbonate is reacted with an orthoester or orthocarbonate in the presence of catalysts to form a prepolymer. Finally, the prepolymer is reacted with a diol in the presence of additional catalysts to yield poly(orthoester carbonates) or poly(orthocarbonate carbonates).

DETAILED DESCRIPTION OF THE INVENTION

The novel and useful polymers of the invention in one embodiment are synthesized by intimately contacting and reacting a monomer polyol with a monomer carbonate to form the corresponding hydroxy substituted carbonate which latter compound is reacted with an ester to yield the polymer.

Exemplary polyols suitable as the reactant monomer include diols, triols and the like that can enter into the polymerization reaction to yield the polymer without adversely effecting the reaction or the polymeric product. The polyols used for the purpose of the invention are known to the art, or they can be prepared by known organic reactions. Generally, the polyols include α,ω-diols, triols and the like of the straight or branched chain type. Representative polyols are alkane polyols having a terminal hydroxyl group at the terminus of an alkylene chain of 3 to 12 carbon atoms. The sequential carbons of the chain also can bear a hydroxyl group. Typical diols include compounds of the formula HO—$R_4(OH)_c$—OH wherein $R_4$ is an alkylene of 3 to 12, and $c$ is 0 to 6. Representative diols named as glycols include 1,5-pentylene glycol; 1,6-hexylene glycol; 1,7-heptylene glycol; 1,8-octylene glycol; 1,9-nonylene glycol; 2,3-dimethylene-1,6-hexylene glycol; 3,6-diehtyl-1,9-nonylene glycol; 1,12-dodecamethylene glycol; and the like.

Polyols containing more than 2 reactive hydroxyl radicals suitable for use herein include polyhydroxyl compounds such as 1,2,3,4,5-hexanehexol; 1,2,3-propanetriol; 1,2,5-pentanetriol; 1,3,5-pentanetriol; 1,2,4-butanetriol; 2-methyl-1,2,3-propanetriol; 2-methyl-2(hydroxymethyl)-1,2-propanediol; 1,4,7-heptanetriol; 1,5,10-decanetriol; 1,5,12-dodecanetriol; and the like.

Other polyols suitable for the purpose of the invention include polyglycols containing the repeating glycol monoether moiety —$CH_2(CH_2)_p$—OH wherein $p$ is 1 to 5, and the polyglycols are diglycols, triglycols, tetraglycols, and the like. Typical polyglycols include diethylene glycol, triethylene glycol, tetraethylene glycol, bis(4-hydroxyethyl)ether, bis(4-hydroxyhexyl)ether, bis(3-hydroxypropyl)ether; and the like.

Additional polyols that can be used in accordance with the invention include polyhydroxyl compounds having 2 or more reactive hydroxyl groups such as pentaerythritol; dipentaerythritol; β-methylglycerol; 1,4-cyclohexane dicarbinol as the cis or trans isomeric configuration, or mixtures thereof; 2,2,4,4-tetramethyl cyclobutane 1,3-diol; adonitol; mannitol; trimethylol propane; sorbitol; penacol; 2-methyl-1,4-cyclohexane dicarbinol; 3-isopropoxy-1,4-cyclohexane dipropanol; 2-ethyl-1,3-cyclopentane dicarbinol; 1,4-phenyldicarbinol; 2-propyl-1,4-phenyldiethanol; 3-butoxy-1,4-phenyldibutanol; 2,3-dimethyl-1,4-benzylol; 1,3-cyclopropanol; 2-propenyl-1,4-cyclohexane dipropanol; and the like. The preparation of the above polyols is well known to the art in *Acta Pharm. Jugaslov.*, Vol. 2, pages 134 to 139, 1952; Ann., Vol. 594, pages 76 to 88, 1955; *J. Am. Chem. Soc.*, Vol. 71, pages 3618 to 3621, 1949; ibid., Vol. 74, pages 2674 to 2675, 1952; *Chem. Abst.*, Vol. 42, pages 8774 to 8775, 1949; ibid., Vol. 43, pages 571 to 573, and 6652, 1949; ibid., Vol. 46, page 9585, 1952, ibid., Vol. 47, page 7575, 1953; ibid., Vol. 48, page 106, 1954; ibid., Vol. 49, pages 6098 to 6099, 1955; *Encyclopedia of Chemical Technology*, Kirk-Othmer, Vol. 10, pages 638 to 678, 1966, published by Interscience Publishers, New York.

Typical monomers having a carbonate unit that can be used for synthesizing the polymers include carbonates of the general formula $(R_5O)_2CO$ wherein $R_5$ is an alkyl, alkenyl or phenyl group. The carbonates include alkylcarbonates, alkenylcarbonates and phenylcarbonates. The alkylcarbonates and alkenylcarbonates can be symmetrical or mixed such as dimethylcarbonate, diethylcarbonate, ethylisopropylcarbonate, dibutylcarbonate, dihexylcarbonate, dioctylcarbonate, dinonylcarbonate, didecylcarbonate, diethenylcarbonate, dipropenylcarbonate, and the like. The carbonates are known to the art and they can be prepared by reacting the corresponding alcohol with carbon monoxide and oxygen at 25° to 45° C under increased pressure of 1 to 4 atmosphere, in the presence of a Lewis acid catalyst and an organic base such as pyridine to yield the corresponding carbonate. The alkylcarbonates also can be prepared by autoclaving an alkylene carbonate with $R_5OH$ in the presence of NaOMe, NaOEt, NaOH or $Na_2CO_3$ catalysts for 2 to 5 hours at 175/1500 psi to give the corresponding carbonate. Methods for preparing the carbonates are described in Ger. Offen. 2,110,194; and in *Chem. Abst.*, Vol. 76, page 99140(z), 1972.

Typical monomers having a carbonate unit also include compounds of the general formula

wherein $R_5$ is an alkyl, alkenyl or phenyl group, and X is a halogen such as fluoro, chloro, and the like. Compounds embraced by the general formula are known to the art and for the purpose of this invention, they are named as formates and carbonates, such as, ethylchlorocarbonate, isopropylchlorocarbonate, butylchlorocarbonate, hexylfluorocarbonate, ethenylchlorocarbonate, and phenylchlorocarbonate. The compounds are known in *Chem. Abst.*, Vol. 43, page 4287(d), 1956; ibid., Vol. 50, page 13081(f), 1956; *J. Am. Chem. Soc.*, Vol. 77, pages 5033 to 5034, 1955; *Chem. Abst.*, Vol. 44, page 3298(i), 1950; and, *J. Am. Chem. Soc.*, Vol. 72, page 1254 to 1263, 1950.

Exemplary starting monomers include compounds of the formula:

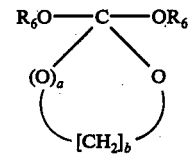

that can react in the polymerization synthesis without adversely affecting it or the polymer. The monomers embraced by the above formula are known to the art, or they can be synthesized by known organic methods. Generally, $R_6$ can be the same or different selected from the group consisting of alkyl, and alkenyl, with $a$ 0 to 1, $b$ is 2 to 6 when $a$ is 0 and $b$ is 2 to 5 when $a$ is 1. The monomers can be simple or mixed, saturated or unsaturated cyclic esters such as, 2,2-dialkoxytetrahydrofuran; 2,2-dialkenyloxytetrahydrofuran; 2,2-dialkoxydihydrofuran; 2,2-dialkenyloxydihydrofuran; 2,2-dialkoxypyran; 2,2-dialkoxy-1-oxepane; 2,2-dialkenyl-1-oxepane; 2,2-dialkoxy-1-oxepane; 2,2-dialkenyloxy-1-oxepane; 2,2-dialkoxy-1,3-dioxolane; 2,2-dialkenyloxy-1,3-dioxolane; 2,2-dialkoxy-1,3-dioxane; 2,2-dialkoxy-1,3-dioxonane; and the like.

Representative of the above monomers include 2,2,5-trimethoxy-3,4-dihydrofuran; 2,2-dimethoxy-1,3-dioxolane; 2,2-diethoxy-1,3-dioxolane; 2,2-dipropoxy-1,3-dioxane; 2,2-diethoxy-6-keto-1,3-dioxane; 2,2-diethoxy-5,5-dimethylpyran; 2,2-diethoxy-5-methyltetrahydrofuran; 2,2-diethenyloxy-5-methyl-tetrahydrofuran; 2,2-diethenyloxy-1,3-dioxolane; 2,2-dipropoxy-1-oxapane; 2,2-dibutoxy-1-oxapane; 2,2-diethenyloxy-1-oxapane; 2-ethoxy-2-propxy-1-oxapane; 2-isopropoxy-2-ethoxy-1,3-dioxonane; 2-ethoxy-2-propenyloxy-1,3-dioxane; and the like.

The above esters can be prepared according to the following preparations: The Pinner synthesis in *Ber.*, Vol. 16, pages 352 to 363, 1883; and ibid., pges 1644 to 1663, 1883; wherein an appropriate nitrile is reacted with an equivalent amount of dry hydrogen halide and an equivalent amount of alcohol to form an iminoester hydrohalide, which is treated with alcohol to form the ester.

The preparation of esters, including the ring types are known to the art with ample description of the methods disclosed in U.S. Pat. Nos. 2,409,699; 2,867,667; 3,323,923; and 3,546,188; and in British Pat. specification Nos. 853,405; and 1,099,559. Also as found in *Synthetic Organic Chemistry*, Chapter 16, pages 542 to 545, 1953 as published by John Wiley and Sons; in *The Chemistry of Aliphatic Orthoesters*, Chapter 2, pages 11 to 43, 1943 published by Reinhold Publishing Corp.; *Encyclopedia of Chemical Technology*, Vol. 8, pages 365 to 383, 1965, Interscience Publishers, New York; *Recueil Trav. Chem. Pays Bes.*, Vol. 88, pages 897 to 904, 1909; *J. Am. Chem. Soc.*, Vol. 64, pages 1825 to 1927, 1942; *Ind. Eng. Chem. Prod. Res. Develop.*, Vol. 10, No. 4, pages 425 to 428, 1971; *J. Am. Chem. Soc.*, Vol. 71, pages 40 to 46, 1949; *Ann. Chem.*, Vol. 65, page 142, 1964; *Angew Chem.*, Vol. 69, page 371, 1957; *J. Am. Chem. Soc.*, Vol. 76, pages 5736 to 5739, 1954; ibid., Vol. 77, pages 5601 to 5506, 1955; *Chem. Ber.*, Vol. 89, page 2060, 1956; *Aust. J. Chem.*, Vol. 17, pages 1385 to 1398, 1964; *Gazz. Chem. Ital*, Vol. 96, page 1164, 1966; *Chem. Commum.*, page 13, 1967; and *Carboxylic Ortho Acid Derivatives*, Chapter 1, pages 1 to 133, 1970, published by Academic Press, New York. The orthoesters can also be prepared by conventional techniques including alcoholysis, condensation, elimination and reduction reactions as described in *Organic Functional Group Preparations*, by Sandler and Karo, Vol. II, Chapter 2, pages 41 to 68, 1971, published by Academic Press.

The novel polymers of the invention are synthesized by intimately contacting and reacting a monomeric substituted halocarbonate with a monomeric polyol to yield the correspondisng substituted hydroxycarbonate. The latter compound is reacted with a cyclic ester to yield in one embodiment an end-capped carbonate that polymerizes in situ in the presence of a catalyst to yield the desired polymer. Generally, the polymerization reaction is carried out by reacting stoichiometric amounts or an excess thereof of each reactant to yield the corresponding product and finally the polymer. For the present purpose, the amount of each reactive monomer present in the reaction can be from about 1 to 10 moles thereof for synthesizing the desired intermediates and polymer.

The reaction of the monomers is carried out in a suitable reactor in separate stages although the actual transesterification and polycondensation continues smoothly from one stage to another. In the first stage, a polyol and a carbonate are reacted under ambient conditions over a period of 1 to 24 hours to form the intermediate hydroxycarbonate. The intermediate is recovered from the reaction medium by extraction with a suitable organic solvent. In the next stage, the intermediate is mixed with an ester and heated to 110° C–130° C in the presence of a catalyst for 1 to 2 hours with distillation of the alkanol formed during the initial transesterification. Then, the remainder of the alkanol is distilled off at elevated temperature at 160° C–180° C and under reduced pressure of 15 mm to 0.01 mm of Hg to yield an end-capped bis(carbonate) monomer intermediate. Finally, the latter intermediate is polymerized at 150° C–200° C in the presence of a catalyst for about 2 to 96 hours to yield the corresponding polymer having the following repeating units

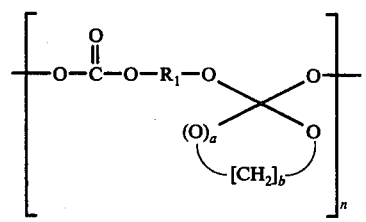

wherein $R_1$, $a$, $b$ and $n$ are as defined.

The polymer is recovered from the reaction vessel by conventional recovery and isolation techniques. In one embodiment, the polymer is isolated from the reactor while still hot by extruding or pouring. In another recovery, the product after cooling, can be dissolved in an organic solvent such as benzene, carbon tetrachloride, methylene chloride, dioxane, toluene, or xylene, followed by the addition thereto of an organic liquid in which the polymer is insoluble, or has limited solubility to precipitate the product. Typical organic liquids for this latter purpose include ether, hexane, pentane, petroleum ether, and hexane-heptane mixtures. The product is finally isolated by filtering and drying under anhydrous conditions. Other methods for recovering the product include lyophilizing from a solvent, and the like.

Representative catalysts suitable for performing the polymerization reaction according to the spirit of the invention include Lewis acid such as boron trifluoride, boron trichloride, boron trichloroetherate, boron trifluoride etherate, stannic oxychloride, phosphorous oxychloride, zinc chloride, phosphorous pentachloride, calcium acetate, antimonous oxide mixture, antimony pentachloride, antimony pentafluoride, stannous octoate, stannic chloride, diethyl zinc, n-butyl lithium, mixtures thereof, and the like. The catalysts also include Bronsted catalysts such as p-toluene sulfonic acid, nitrobenzene sulfonyl chloride, polyphosphoric acid, crosslinked polystyrene sulfonic acid, acidic silica gel, and mixtures thereof. Other catalysts include basic catalysts such as tetrabutyl titanate, ester interchange catalysts of the formulas $M[Al(OR_7)_4]$, $M[HZr(OR_5)_6]_2$, $MH[Ti(OR)_5]$, and $N[Ti(OR_5)_6]$ wherein M represents an alkali metal, N represents an alkaline earth metal, and $R_7$ represents an alkyl or aryl. The amount of catalyst used is about one part catalyst to about 100 parts of ester or bis(carbonate) monomer. Smaller or larger amounts can also be used, such as 0.0005% to about 0.01% based on the weight of ester or bis(carbonate) monomer. Usually, the addition of trace amounts of catalyst will provide sufficient catalyst for successfully carrying out the reactions. Optionally, the same catalyst can be used in the transesterification and polycondensation steps, or a different one can be used in each step for an interrupted or continuous polymerization.

The polymerization including the transesterification and polycondensation stages, can optionally be carried out in the presence of an added inert organic solvent that does not adversely effect the reactions, or the reactions can proceed in the absence of added inert solvent. In the latter embodiment, one of the reactants, for example the polyol monomer, initially serves as the solvent medium. As transesterification proceeds, liquid by-product can act as solvent and it is removed by distillation, usually with the assist of heat and vacuum. Liquid formed during the reaction also can be removed from the reaction vessel by conventional, continuous, or periodic azeotropic distillation, or the solvent can be distilled under vacuum. Suitable azeotropic solvents are innocuous solvents including toluene, benzene, m-xylene, cumene, pyridine, and n-heptane.

The term alkylene appearing above and used elsewhere in this specification denotes a straight or branched chain divalent alkylene radical of 1 to 10 carbon atoms inclusive, such as methylene, 1,2-ethylene; 1,3-propylene; 1,1-propylene; 1,4-butylene; 1,5-pentylene; 2,5-hexylene; 1,6-hexylene; 1,7-heptylene; 2-methyl-1,7-heptylene; 1,8-octylene; 2-isopropoxy-1,10-decylene; 1,10-decylene; 3-propenyl-1,10-decylene; 2-propyl-1,6-hexylene; 1,1-dimethyl-1,6-hexylene; and the like.

The term alkenylene as used according to the invention includes a straight or branched chain divalent radical having 2 to 10 carbon atoms, such as 1,3-prop-1-enylene; 1,4-but-1-enylene; 1,4-but-2-enylene; 1,5-pent-1-enylene; 1,6-hex-2-enylene; 1,7-hept-2-enylene; 1,8-oct-2-enylene; 1,9-non-2-enylene; 3-methyl-(1,10-dec-2-enylene); 4-propyl-(1,6-hex-2-enylene); 5-methoxy-(1,6-hex-2-enylene); 2-propenyl-(1,6-hex-4-enylene) and the like.

The term alkyleneoxa used herein denotes a straight or branched chain bivalent alkyleneoxa of 2 to 20 carbons with an oxa bridging atom between alkylene groups such as dimethyleneoxa; diethyleneoxa; dipropyleneoxa; dibutyleneoxa; diisopropyleneoxa; dihexyleneoxa; dioctyleneoxa; didecyleneoxa; and the like. The term alkenyloxa includes straight or branched chain bivalent alkenyleneoxa of 4 to 20 carbons with an oxa bridging atom between alkenylene groups including diprop-1-enyleneoxa; dibut-1-enyleneoxa; dipent-2-enyleneoxa; dihex-3-enyleneoxa; and the like.

The term cycloalkylene as used for $R_1$ includes monocyclic, divalent cycloalkylene rings of 3 to 7 carbons such as cyclopropylene; cyclobutylene; cyclopentylene; cyclohexylene; and cycloheptylene. Similarly, the phrase cycloalkylene substituted with an alkyl, alkylene, alkoxy, alkenyl or alkenylene includes substituted cycloalkylenes such as 2-methyl-1,3-cyclopropylene; 2-methyl-1,4-cyclopentylene; 2-methyl-1,6-cyclohexylene; 2-ethoxy-2,3-cyclopropylene; 5-butoxy-1,4-cyclopentylene; 2-methoxy-1,4-cyclohexylene; 2-propenyl-1,5-cyclopentylene; 2-isobutenyl-1,6-cyclohexylene; 1,4-cyclohexyl-dimethylene; 1,4-cyclohexyl-diethenylene; 3,5-cyclopentyl-diethylene; and the like.

Exemplary cycloalkenylene and cycloalkenylene substituted with an alkyl, alkylene, alkoxy, alkenyl or alkenylene include divalent monocyclic cycloalkenylene rings having 5 to 7 carbons as ring members such as 1,4-cyclopent-2-enylene; 1,5-cyclopent-3-enylene; 1,6-cyclohex-2-enylene; 1,5-cyclohex-2-enylene; and substituted rings such as 5-methyl-(1,4-cyclopent-2-enylene); 6-ethyl-(1,4-cyclohex-2-enylene); 6-ethoxy-(1,5-cyclohex-2-enylene); 2-propyl-(1,5-cyclohex-3-enylene); 2-methoxy-(1,4-cyclohex-2-enylene); 2-allyl-(1,4-cyclohept-2-enylene); 2-methoxy-(1,4-cyclohept-2-enylene); 1,4-cyclopent-2-enyl dimethylene; 1,4-cyclohex-2-enyl dipropenylene; and the like.

The term alkyl appearing herein embraces straight and branched chain alkyl radicals of 1 to 10 carbons such as methyl, ethyl, no-propyl, n-butyl, t-butyl, n-amyl, n-hexyl, n-heptyl, n-ortyl, n-decyl; and the like. Also, the various positional isomers such as isopropyl, isobutyl, sec-butyl, isoamyl, isohexyl, t-heptyl, and the like.

The term arylene includes phenylene and arylene substituted with alkyl, alkylene, alkenyl, alkenylene and alkoxy and includes arylene of 6 to 26 carbons total when alkyl is 1 to 10 carbons, alkylene is 1 to 10 carbons, alkenyl is 2 to 10 carbons, alkenylene is 2 to 10 carbons, and alkoxy is 1 to 10, such as 2-methyl-1,4-phenylene; 3-methoxy-1,4-phenylene; 2-propyl-1,4-phenylene; and the like.

Exemplary alkenyls as used in this application include straight and branched chain lower alkenyl groups of 2 to 10 carbons such as 1-propenyl, 2-propenyl or allyl, 1-butenyl, 2-butenyl, 1-pentyl, 2-hexenyl, and the corresponding positional isomers thereof such as 1-isobutenyl; 2-isobutenyl; 2-sec-butenyl; 2-methyl-1-butenyl; 2-methyl-2-pentenyl; 2,3-dimethyl-3-hexenyl; and the like.

The term alkoxy used by this invention includes the straight and branched chain lower alkoxy groups and the positional isomers thereof having 1 to 10 carbon atoms. For example, methoxy, ethoxy, propoxy, butyoxy, n-pentoxy, n-hexoxy, isopropoxy, 2-butoxy, isobutyoxy, 3-pentoxy, and the like.

The following examples are set forth as representative examples of preparing the polymers of the invention. These examples are not to be construed as limiting the scope of the invention, as these and other functionally equivalent means will be readily apparent to those skilled in the subject art in the light of the present disclosure.

DETAILED DESCRIPTION OF EXAMPLES

EXAMPLE 1

To a solution of the polyol 1,6-hexane diol, 94.5 g, 0.8 mole, and pyridine, 100 ml, was added the carbonate ethyl chloroformate, 21.7 g, 0.2 mole, dropwise over a 1 hour period with some external cooling to maintain the temperature at 20° to 25° C. After 3 hours at room temperature, the reaction mixture was poured into 1 liter of benzene in a 2 liter separating funnel. It was then extracted 7 times with deionized water and the benzene extract dried over anhydrous $Na_2SO_4$. The benzene was removed by evaporation under reduced pressure, and the residue purified by fractional distillation under reduced pressure. The boiling point was 110° to 111° C/0.05 mm Hg.

Next, to the above hydrocarbonate intermediate was added the ester 2,2-diethoxytetrahydrofuran and the reactants heated at 130° C in the presence of polyphosphoric acid catalyst. The by-product ethanol was distilled off by raising the temperature to 180° C and under a reduced pressure of 0.03 mm Hg. The acid catalyst was neutralized by the addition of NaOBu to yield a prepolymer, the end-capped bis(carbonate) prepolymer. Finally, the end-capped prepolymer was polymerized in situ at 150° to 175° C in the presence of added excess diol, and the catalyst $NaTiH(OBu)_6$, to yield the polymer. The reaction steps leading to the polymer are seen in the accompanying flow-chart and from the following wherein $n$ is 10 to 2,000:

-continued

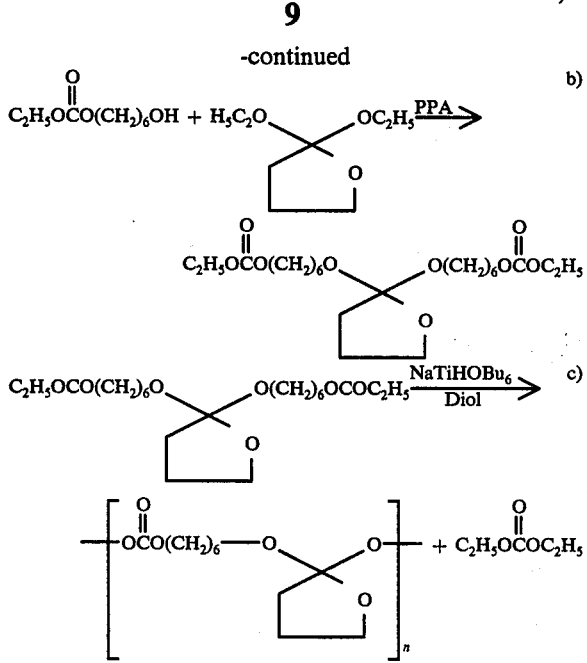

EXAMPLE 2

To a solution of 1,6-hexane diol, 94.5 g, 0.8 mole, and pyridine, 100 ml, was added ethyl chloroformate, 21.7 g, 0.2 mole, dropwise over a 1 hour period with some external cooling to keep the temperature at 20° to 25° C. After 3 hours of mixing at room temperature, the reaction mixture was poured into one liter of benzene in a separating funnel and extracted 7 times with deionized water. The benzene extract was dried over anhydrous $Na_2SO_4$, with the benzene removed by evaporation under reduced pressure. Next, the residue was purified by fractional distillation under reduced pressure to yield the intermediate with a boiling point of 110° to 111° C/0.05 mm Hg.

Next, the above intermediate was mixed with half the amount on a mole ratio of 2,2-diethoxy-1-oxane and heated to 130° to 135° C in the presence of polyphosphoric acid, with the alkanol formed distilled off at 180° C and under a vacuum of 0.03 mm Hg. The acid catalyst was neutralized with sodium butoxide to yield the end-capped bis(oxane carbonate) monomer. Finally, the monomer was polymerized in situ at 150° to 175° C in the presence of sodium hydrogen titanium hexabutoxide to yield the polymer of the following structure, wherein $n$ is greater than 10:

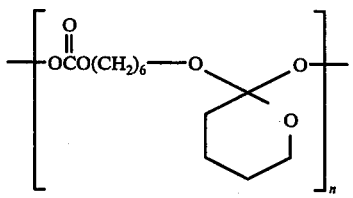

EXAMPLES 3 – 7

The procedure of Example 1 is repeated herein, with all reaction conditions as previously described, except 2,2-diethoxy-1-oxane is replaced by the monomers listed below:

2,2-dipropoxy-2-oxepane;
2,2-dibutoxy-1-oxocane;
2,2-diethoxy-1,3-dioxolane;
2,2-diethenyloxy-1,3-dioxane; and
2,2-diethoxy-1,3-dioxonane;

to yield the following polymers, wherein $n$ is 10 or greater:

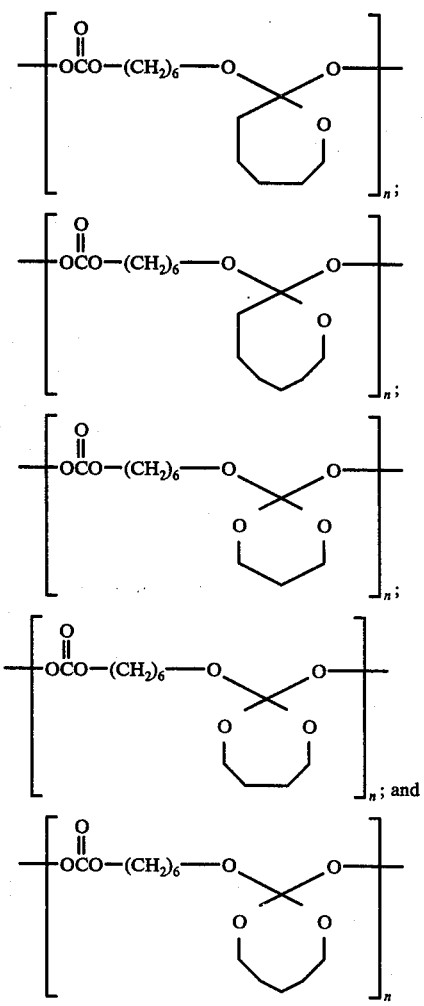

EXAMPLE 8

To a solution of 1,4-cyclohexane dicarbinol, 1 mole, and 100 ml of pyridine is added dropwise over an hour, 0.3 mole of ethyl chloroformate with the addition temperature held at 20° to 25° C. After 3 hours of stirring under ambient conditions, the reaction mixture is mixed with a liter of benzene and extracted 5–7 times with deionized water. The benzene extract containing the intermediate is dried over anhydrous sodium sulfate and the benzene removed under vacuum. Next, the residue was purified by fractional distillation under reduced pressure to yield the intermediate.

Next, the above intermediate is mixed with half the amount on a mole ratio of 2,2-diethoxytetrahydrofuran and heated to 130° to 135° C in the presence of p-toluene sulfonic acid, with the alkanol of reaction distilled over at 180° to 185° C and under 0.03 mm Hg. Then, the acid catalyst was neutralized with sodium butoxide to yield the end-capped bis(tetrahydrofuran carbonate) monomer. Finally, the monomer was polymerized in situ at 150° to 175° C in the presence of the ester interchange catalyst sodium hydrogen titanium hexabutoxide to yield the polymer prepared by the following reaction steps:

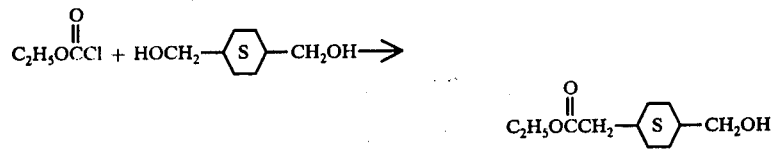

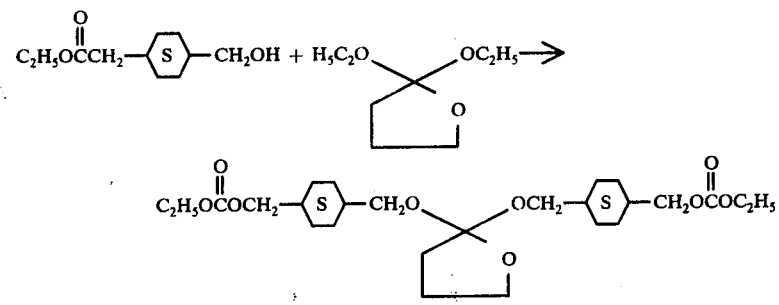

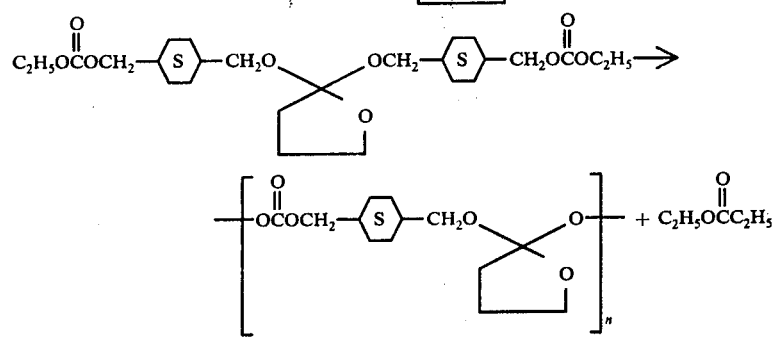

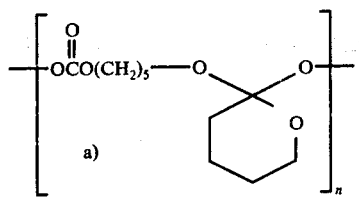

a)

b)

c)

EXAMPLES 9 – 11

Repeating the procedure of Example 1 with all reaction conditions as previously set forth, except the monomeric pairs of the example are replaced by the following:

1,10-decane diol and 2,2-diethoxy-1,3-dioxolane;
1,4-butane diol and 2,2-diethoxy-1-oxepane; and
1,5-pentane diol and 2,2-dihexoxy-1-pyran;

the following polycarbonates are produced, wherein $n$ is greater than 10:

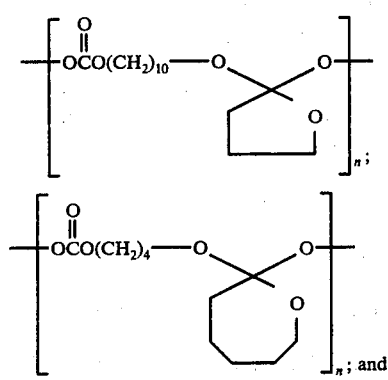

EXAMPLE 12

To one equivalent of 2-ethyl-1,4cyclohexane dicarbinol in 150 ml of pyridine is added 0.5 equivalent of propyl chloroformate dropwise over 1½ hours with some external cooling to keep the temperature at 20° to 25° C. Next, the reactants are mixed for 3 to 4 hours under normal atmospheric pressure at 23° to 25° C to form the intermediate:

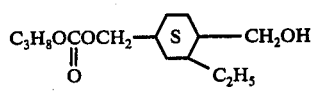

The intermediate is recovered by pouring the reaction medium into a liter of benzene and extracting unreacted dicarbinol and chloroformate with water. The benzene extract containing the intermediate is dried over anhydrous $Na_2SO_4$ with the benzene removed by evaporation under reduced pressure. Next, the residue is purified by fractional distillation under reduced pressure to yield the intermediate.

Next, the above intermediate is mixed with 2,2-dimethoxy-5-methyl-1,3-dioxalane and heated to 135° C in the presence of polyphosphoric acid for 2 to 3 hours, then to 180° C with methanol distilled at 180° C and under a vacuum of 0.01 mm Hg. The acid catalyst is neutralized with sodium butoxide to yield:

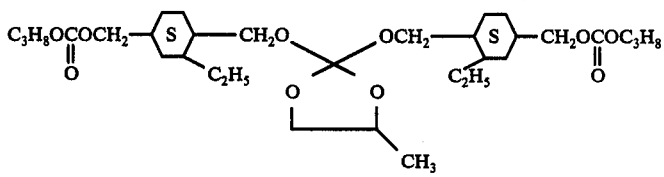

Finally, the end-capped monomer is polymerized at 160 to 175° C in the presence of trace amounts of sodium hydrogen titanium hexabutoxide to yield the polymer as follows:

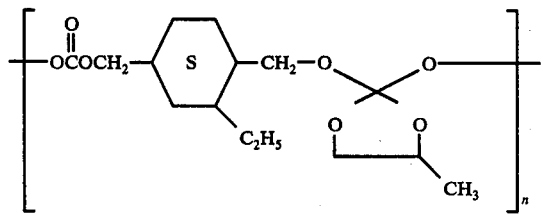

EXAMPLES 13 - 15

The procedure of Example 12 is repeated herein and the monomers and polymers produced are as follows:

2 hour period with the temperature of the addition flask kept at 25° C. Next, the reactants are mixed under normal atmospheric pressure, at 23° to 25° C for 3 to 4 hours to yield the intermediate carbonate:

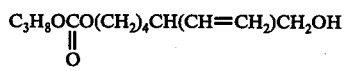

The carbonate was recovered by extraction with benzene followed by washing with water. The benzene containing the intermediate is dried over anhydrous $Na_2SO_4$ with excess benzene removed under lowered pressure. Finally, the residue is purified by fractional distillation under reduced pressure to yield the intermediate.

Next, the carbonate is mixed with 2,2-dimethoxy-1,3-dioxalane and the ingredients heated to 135° to 140° C in the presence of a catalyst composition comprising p-toluene sulfonic acid and polyphosphoric acid for 3½ to 4½ hours, followed by a temperature rise to 180° C with

| MONOMER | MONOMER | POLYMER |
|---|---|---|
| a) HO—(CH$_2$)$_{10}$—OH | (structure) | (structure) |
| b) HO(CH$_2$)$_2$CHCH$_3$(CH$_2$)$_3$OH | (structure) | (structure) |
| c) HO—(CH$_2$)$_8$—OH | (structure) | (structure) |

EXAMPLE 16

To an equivalent of 2-ethenyl hexamethylene 1,6-diol HO(CH$_2$)$_4$CH(CH=CH$_2$)CH$_2$OH in 150 ml of pyridine is added 0.5 equivalent of propyl chloroformate over a distillation of the by-product methanol under a vacuum of 0.01 to 0.02 mm Hg. The acid catalyst is neutralized to yield the symmetrical end-capped carbonate monomer of the following structure:

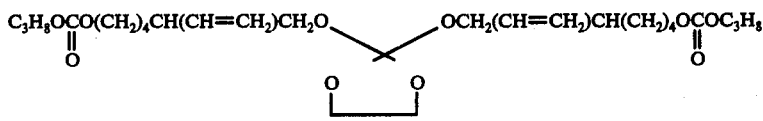

The polymerization of the latter monomer is carried out at 165° to 170° C in the presence of small amounts of sodium hydrogen titanium hexabutoxide to yield the polymer of the following structure:

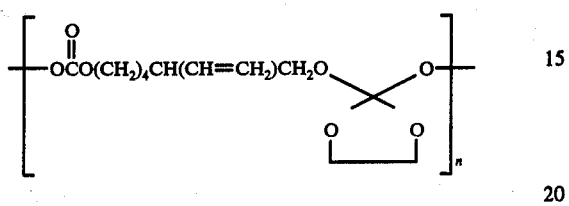

EXAMPLE 17

To an equivalent of diethylene glycol of the formula $HOCH_2CH_2OCH_2CH_2OH$ is added 0.2 equivalent of dialkylcarbonate of the formula $(C_2H_5O)_2CO$ in pyridine and the reactants stirred for several hours. The carbonate formed is isolated by extraction and washing with water as previously described in Example 2, to yield the intermediate of the following structural formula:

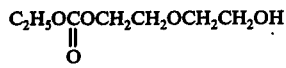

Next, the ethyl diethylene glycol carbonate is mixed with an equivalent of 2,2-diethoxytetrahydrofuran, with trace amounts of polyphosphoric acid and the reactants heated to 130° C with continuous distillation of ethanol. Then, the temperature is raised to 180° C, and the pressure lowered to 0.03 mm Hg with the remainder of the ethanol distilled off over a 1½ to 2 hour period. The acid catalyst is neutralized to yield the symmetrical bis(carbonate) of the following structural formula:

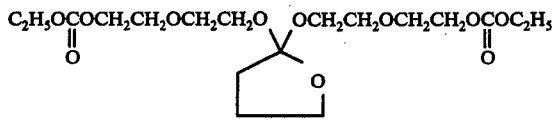

The bis(carbonate) is polymerized according to Example 2 to yield the polymer of the structural formula:

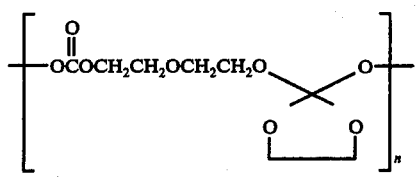

EXAMPLE 18

To an equivalent of diethylene glycol of the formula $HO-CH_2CH_2OCH_2CH_2OH$ is added 0.5 equivalent of diethylcarbonate in pyridine and the procedures of Examples 1 and 18 followed to yield:

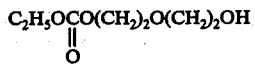

Then, the ethyl diethylene glycol carbonate is reacted with 2,2-diethoxy-$\Delta^3$-oxepine in the presence of catalyst to yield the following compound:

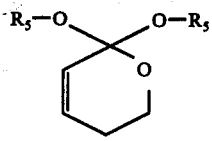

wherein $R_5$ is:

The compound is polymerized according to Examples 1 and 17 to yield the polymer of the following formula where $n$ is 10 to 1000:

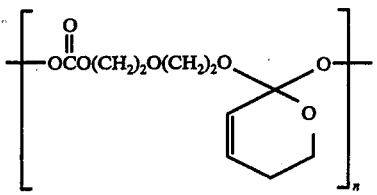

EXAMPLE 19

To an equivalent of phenylene 1,4-diol of the formula

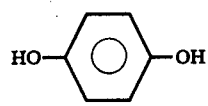

is added 0.5 equivalent of dipropylcarbonate and the procedures of Examples 1 and 17 followed to yield ethylphenyl carbonate as follows:

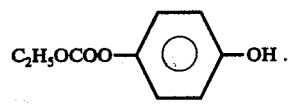

Next, the carbonate is reacted with 2,2-diethoxy-tetrahydrofuran to yield the following compound:

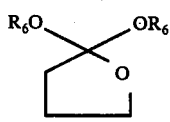

wherein $R_6$ is:

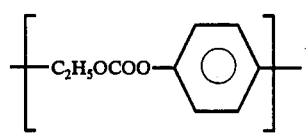

The latter compound is polymerized according to the previously described examples to yield the following polycarbonate where $n$ is 10 to 1000:

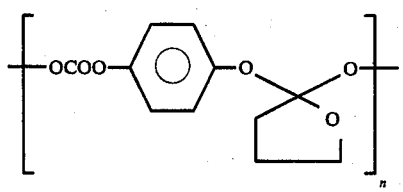

The polymers prepared according to the invention are useful for making slow release fertilizers. The fertilizers are coated in their conventional form such as granules, powder, beads, and the like. Fertilizers that can be coated include urea, fertilizers with slow ammonia release, fertilizers in the form of water soluble salts such as elements of carbon, nitrogen, phosphorous, sulfur, potassium, calcium, magnesium, manganese, zinc, copper, boron and the like. Also, fertilizers such as the common fertilizers designated by 8-24-12, 8-8-6, 5-20-20, 12-12-12, 14-16-0, 8-4-6, 3-9-6, and the like. Additionally, the fertilizer or plant nutrient can be impregnated into, or suitably admixed with inert materials such as silica, coke, and the like.

In one embodiment, the polymers prepared according to the spirit of the invention are applied to the fertilizers, for example, in granular form, by mixing in a fluidized bed having a conical bottom. The bed is equipped with an air inlet at the top for introducing air for mixing the polymer and fertilizer until the fertilizer is coated with 1 to 10% weight of polymer. The temperature of the air is dependent on the concentration of the dispersion, usually 20° to 100° C. In another embodiment, the fertilizer is coated by mixing the polymer with an organic solvent to facilitate its application in thin coat form to the fertilizer granules. The selection of suitable solvents, in view of those set forth above, is within the skill of the art. The coating compositions can additionally contain pigments, dyes, driers, stabilizers, and the like. The polymers of the invention also can be used for coating medicines for administering to the digestive tract where the therapeutic value of the medicine is obtained.

The polymeric materials embodying the invention can be produced batch-wise or in continuous fashion, and the polymers can be used alone or in admixture with similar or dissimilar polymeric materials. The polymers can be pressed, extruded, spun, injected molded, extrusion molded, and the like by known polymer manufacturing methods.

While the invention pertains to polymers, and while these polymers and the method for making them have been described in detail for the now preferred embodiments, those skilled in the art will appreciate that various modifications, changes, additions and omissions in the invention can be made without departing from the spirit of the invention.

We claim:

1. A copolymer of the general formula:

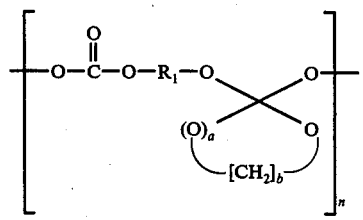

wherein $R_1$ is a member selected from the group consisting of alkylene of 1 to 10 carbons; alkenylene of 2 to 10 carbons; alkyleneoxa of 2 to 20 carbons; alkenyleneoxa of 4 to 20 carbons; cycloalkylene of 3 to 7 carbons; cycloalkylene of 3 to 7 carbons substituted with alkyl of 1 to 10 carbons, alkylene of 1 to 10 carbons, alkenyl of 2 to 10 carbons, alkenylene of 2 to 10 carbons, and alkoxy of 1 to 10 carbons; cycloalkenylene of 5 to 7 carbons; cycloalkenylene of 5 to 7 carbons substituted with an alkyl of 1 to 10 carbons, alkylene of 1 to 10 carbons, alkenyl of 2 to 10 carbons, cycloalkenylene of 2 to 10 carbons, and alkoxy of 1 to 10 carbons; arylene; and arylene of 6 to 26 carbons substituted with an alkyl of 1 to 10 carbons, alkylene of 1 to 10 carbons, an alkenyl of 2 to 10 carbons and alkoxy of 1 to 10 carbons; and wherein $a$ is 0 to 1, $b$ is 2 to 6 when $a$ is 0, $b$ is 2 to 5 when $a$ is 1, and $n$ is at least 10.

2. A polymer according to claim 1 of the following formula wherein $c$ is a positive integer of 1 to 10:

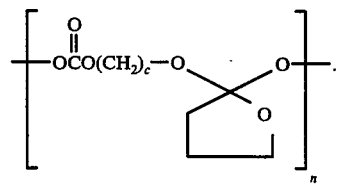

3. A polymer according to claim 1 of the following formula wherein $c$ is a positive integer of 1 to 10:

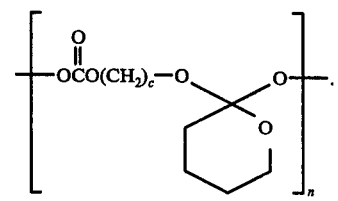

4. A polymer according to claim 1 of the following formula wherein $c$ is a positive integer of 1 to 10:

5. A polymer according to claim 1 of the following formula wherein c is a positive integer of 1 to 10:

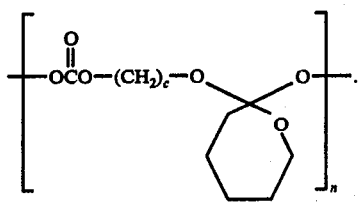

6. A polymer according to claim 1 of the following formula wherein c is a positive integer of 1 to 10:

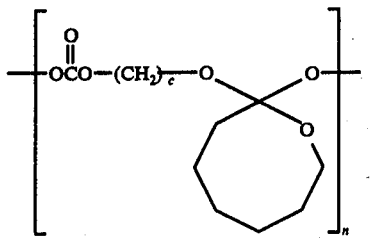

7. A polymer according to claim 1 of the following formula wherein c is a positive integer of 1 to 10:

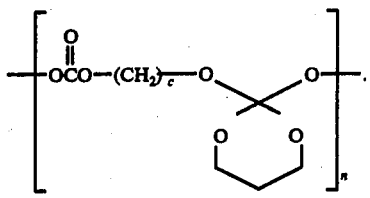

8. A polymer according to claim 1 of the following formula wherein c is a positive integer of 1 to 10:

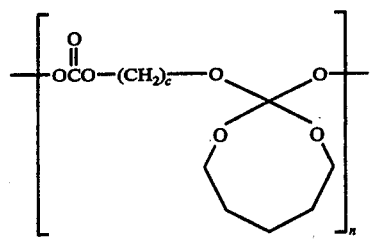

9. A polymer according to claim 1 of the following formula:

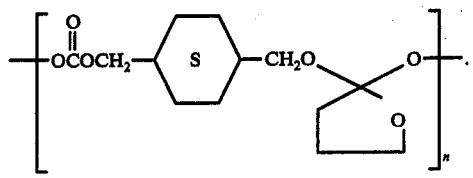

10. A polymer according to claim 1 of the following formula:

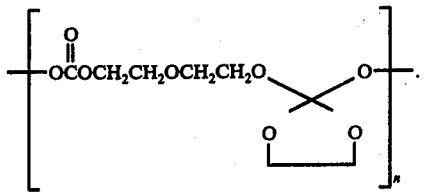

11. A polymer according to claim 1 of the following formula:

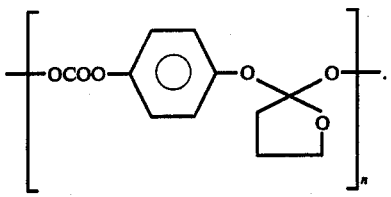

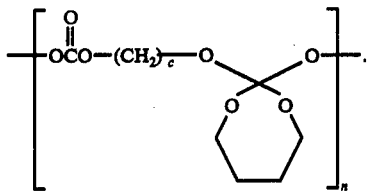

* * * * *